United States Patent
Otts

(10) Patent No.: US 10,918,476 B2
(45) Date of Patent: Feb. 16, 2021

(54) ELECTROWETTING INTRAOCULAR LENS WITH ISOTONIC AQUEOUS PHASE

(71) Applicant: Verily Life Sciences LLC, Mountain View, CA (US)

(72) Inventor: Daniel Otts, Pleasanton, CA (US)

(73) Assignee: Verily Life Sciences LLC, Mountain View, CA (US)

(*) Notice: Subject to any disclaimer, the term of this patent is extended or adjusted under 35 U.S.C. 154(b) by 146 days.

(21) Appl. No.: 15/870,208

(22) Filed: Jan. 12, 2018

(65) Prior Publication Data

US 2018/0280135 A1    Oct. 4, 2018

Related U.S. Application Data

(60) Provisional application No. 62/478,956, filed on Mar. 30, 2017.

(51) Int. Cl.
*A61F 2/16*     (2006.01)
*G02B 3/14*     (2006.01)
(Continued)

(52) U.S. Cl.
CPC .......... *A61F 2/1635* (2013.01); *A61F 2/1627* (2013.01); *A61F 2/1637* (2013.01);
(Continued)

(58) Field of Classification Search
CPC .... A61F 2/1635; A61F 2/1627; A61F 2/1637; A61F 2250/0002; A61F 2250/0003;
(Continued)

(56) References Cited

U.S. PATENT DOCUMENTS

| | | |
|---|---|---|
| 8,382,280 B2 | 2/2013 | Gupta et al. |
| 8,390,939 B2 | 3/2013 | Henriksen et al. |

(Continued)

FOREIGN PATENT DOCUMENTS

| | | |
|---|---|---|
| WO | 2007107589 A1 | 9/2007 |
| WO | 2012166948 A1 | 12/2012 |
| WO | 2016182716 A1 | 11/2016 |

OTHER PUBLICATIONS

Mugele et al., "Electrowetting: from basics to applications", Topical Review, Journal of Physics: Condensed Matter, Published Jul. 1, 2005.
(Continued)

*Primary Examiner* — David H Willse
*Assistant Examiner* — Tiffany P Shipmon
(74) *Attorney, Agent, or Firm* — McDonnell Boehnen Hulbert & Berghoff LLP

(57) ABSTRACT

An eye-implantable device including an electrowetting lens is provided that can be operated to control an overall optical power of an eye in which the device is implanted. A lens chamber of the electrowetting lens contains first and second fluids that are immiscible with each other and that differ with respect to refractive index. By applying a voltage to electrodes of the lens, the optical power of the lens can be controlled by affecting the geometry of the interface between the fluids. One of the fluids is an aqueous fluid that is isotonic relative to the aqueous humor of the eye to prevent flux of water into or out of the lens chamber. Thus, the lens chamber may be composed of water-permeable materials. Such water-permeable materials may be flexible, to permit the lens to be folded into a smaller profile during implantation.

18 Claims, 6 Drawing Sheets

(51) Int. Cl.
 G02B 1/14 (2015.01)
 G02B 26/00 (2006.01)
 G02C 7/08 (2006.01)
 G02B 1/04 (2006.01)
(52) U.S. Cl.
 CPC .............. *G02B 1/043* (2013.01); *G02B 1/14* (2015.01); *G02B 3/14* (2013.01); *G02B 26/004* (2013.01); *G02B 26/005* (2013.01); *G02C 7/085* (2013.01); *A61F 2250/0002* (2013.01); *A61F 2250/0003* (2013.01); *A61F 2250/0053* (2013.01); *A61F 2250/0056* (2013.01); *G02B 2207/115* (2013.01)
(58) Field of Classification Search
 CPC ... A61F 2250/0053; G02B 1/14; G02B 1/043; G02B 3/14; G02B 26/004; G02B 26/005; G02C 7/085
 See application file for complete search history.

(56) References Cited

U.S. PATENT DOCUMENTS

| | | | |
|---|---|---|---|
| 8,460,376 | B2 | 6/2013 | Donitzky et al. |
| 8,665,526 | B2 | 3/2014 | Pugh et al. |
| 2008/0137213 | A1 | 6/2008 | Kuiper et al. |
| 2013/0229618 | A1 | 9/2013 | Otts et al. |
| 2013/0258277 | A1 | 10/2013 | Pugh et al. |
| 2014/0228949 | A1* | 8/2014 | Argento ............... B29D 11/026 623/6.13 |
| 2014/0253870 | A1 | 9/2014 | Jiang et al. |
| 2015/0043085 | A1 | 2/2015 | Tsuji |
| 2016/0058553 | A1* | 3/2016 | Salahieh ............... A61F 2/1629 623/6.13 |
| 2016/0331518 | A1* | 11/2016 | Cable, II ................. A61F 2/16 |

OTHER PUBLICATIONS

B. Berge, "Liquid Lens Technology: Principle of Electrowetting Based Lenses and Applications to Imaging", IEEE, 2005, pp. 227-230.

Lu et al., "Tunable dielectric liquid lens on flexible substrate", Applied Physics Letters 103, 2013.

Mallin, "Flexible Membrane Liquid Lens", Optics & Optoelectronics, 2011 NNIN REU Research Accomplishments.

Li et al., "Fabrication and Characterization of Flexible Electrowettingon Dielectrics (EWOD) Microlens", NIH Author Manuscript, 2014, 432-441.

Li et al., "Electrowetting-driven variable-foxus microlens on flexible surfaces", Applied Physics Letters 100, 2012.

International Search Report and Written Opinion of International Application No. PCT/US2018/017097 dated May 15, 2018.

* cited by examiner

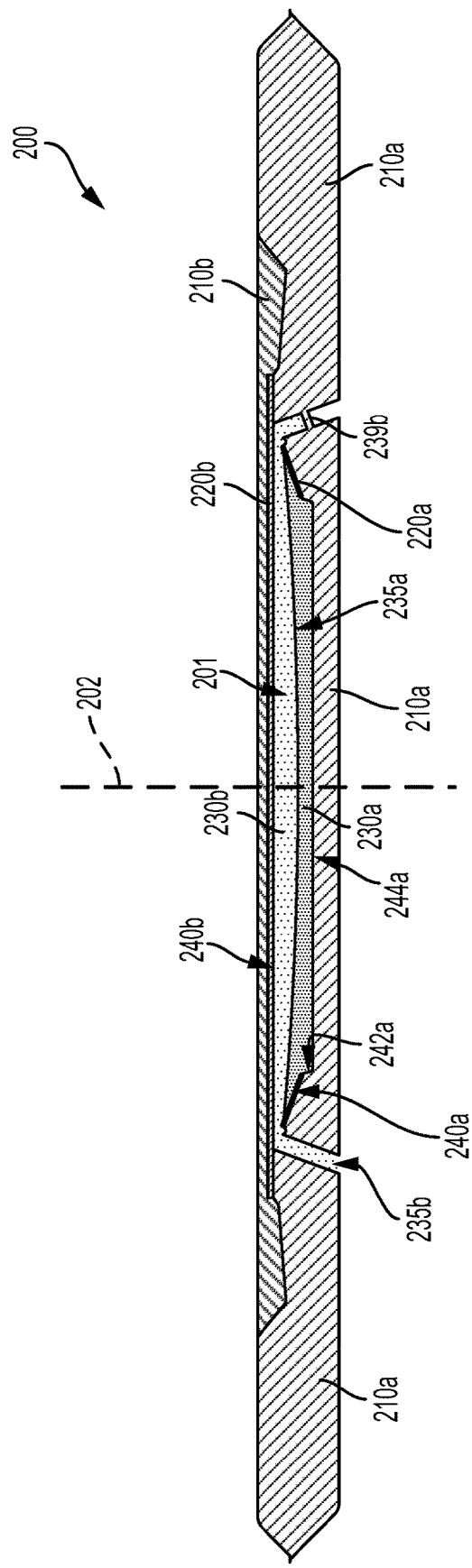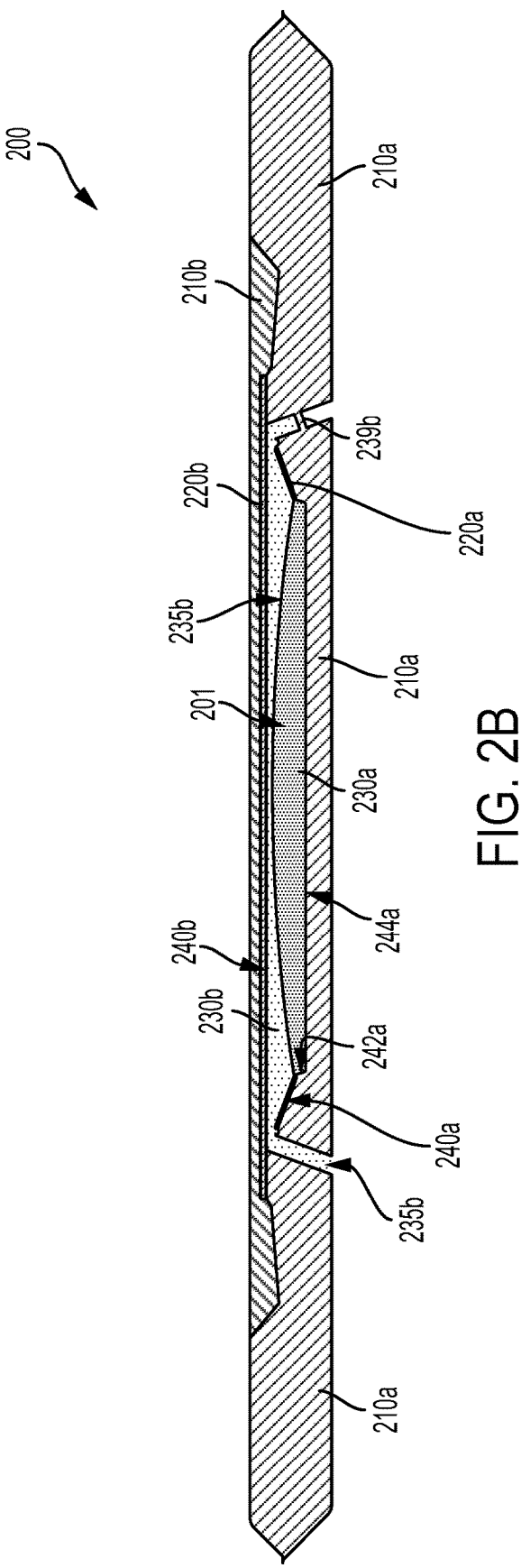

ELECTROWETTING INTRAOCULAR LENS WITH ISOTONIC AQUEOUS PHASE

CROSS-REFERENCE TO RELATED APPLICATION

This application claims priority to U.S. Provisional Patent Application No. 62/478,956, filed Mar. 30, 2017, which is incorporated herein by reference.

BACKGROUND

Unless otherwise indicated herein, the materials described in this section are not prior art to the claims in this application and are not admitted to be prior art by inclusion in this section.

Devices can be provided on the surface of the eye and/or within the eye to provide a variety of functions. In some examples, these functions can include functions to improve the ability of a person to view their environment (e.g., to provide an optical correction, to stimulate the retina directly) and/or to present additional visual information to the person (e.g., to present a heads up display or other indications to the person). Additionally or alternatively, these functions can include detecting a property of the body of a person (e.g., a blood glucose level, a concentration of an ion in the blood, a desired optical power of the eye) via the eye, e.g., by detecting forces, concentrations of analytes, electrical fields, or other properties related to the property of interest. Such functions can be provided by an intraocular device implanted within the eye (e.g., a retinal implant configured to stimulate the retina to restore vision, a device implanted within the lens capsule to provide a static and/or controllable optical power to the eye).

Such an eye-implantable device could include an electronically actuated lens to provide a controllable amount of optical power to the eye. An electronically actuated lens could include a lens chamber that contains two or more immiscible fluids whose geometry within the lens chamber can be electronically controlled in order to control an overall optical power of the lens.

The design and fabrication of such an eye-implantable device could be subject to a variety of mechanical, optical, electrical, chemical, and biochemical constraints. For example, materials of the eye-implantable device may be biocompatible, flexible, optically clear and/or having a specified refractive index, and/or have one or more further specified qualities. It may also be beneficial to fabricate such an eye-implantable device such that a lens chamber of a lens of the device is hermetically sealed. Such a hermetic seal could be provided to prevent water from passing between one or more aqueous fluids within the lens and the aqueous humor of the eye. Such passage of water could result in changes in the pressure and/or volume of the lens, causing damage to the lens, changes in the optical power of the lens, or other unwanted effects. It can be difficult to construct an eye-implantable device to maintain such a hermetic seal, to be able to be folded for implantation, to have one or more specified optical, mechanical, electrical, biochemical, or other properties, and/or to satisfy some additional constraints.

SUMMARY

Some embodiments of the present disclosure provide an eye-implantable device that includes an electrowetting lens. The electrowetting lens includes: (i) a polymeric material that is permeable to water in an aqueous humor of a human eye; (ii) a lens chamber, wherein the polymeric material defines at least a portion of the lens chamber; (iii) a first fluid disposed in the lens chamber, wherein the first fluid includes an aqueous solution having an osmolality corresponding to an osmolality of the aqueous humor; (iv) a second fluid disposed in the lens chamber, wherein the second fluid is immiscible with the first fluid, and wherein a refractive index of the second fluid differs from a refractive index of the first fluid; (v) a first electrode, wherein the first electrode is disposed on an internal surface of the lens chamber in contact with the first fluid; and (vi) a second electrode, wherein the second electrode is disposed on an internal surface of the lens chamber in contact with at least one of the first fluid or the second fluid, wherein the second electrode includes a dielectric coating.

Some embodiments of the present disclosure provide an eye-implantable device that includes an electrowetting lens. The electrowetting lens includes: (i) a polymeric material that is permeable to water in an aqueous humor of a human eye; (ii) a lens chamber, wherein the polymeric material defines at least a portion of the lens chamber; (iii) a first fluid disposed in the lens chamber, wherein the first fluid includes an aqueous solution having an osmolality corresponding to an osmolality of the aqueous humor; (iv) a first electrode, wherein the first electrode is disposed on an internal surface of the lens chamber in contact with the first fluid; and (v) a second electrode, wherein the second electrode is disposed on an internal surface of the lens chamber in contact with the first fluid, wherein the second electrode includes a dielectric coating.

Some embodiments of the present disclosure provide a method including: (i) forming an incision through a cornea of an eye; (ii) inserting an eye-implantable device into the eye through the incision; and (iii) placing the eye-implantable device at a specified location within the eye. The eye-implantable device includes an electrowetting lens. The electrowetting lens of the eye-implantable device includes: (a) a polymeric material that is permeable to water in an aqueous humor of the eye; (b) a lens chamber, wherein the polymeric material defines at least a portion of the lens chamber; (c) a first fluid disposed in the lens chamber, wherein the first fluid includes an aqueous solution having an osmolality corresponding to an osmolality of the aqueous humor; (d) a second fluid disposed in the lens chamber, wherein the second fluid is immiscible with the first fluid, and wherein a refractive index of the second fluid differs from a refractive index of the first fluid; (e) a first electrode, wherein the first electrode is disposed on an internal surface of the lens chamber in contact with the first fluid; and (f) a second electrode, wherein the second electrode is disposed on an internal surface of the lens chamber in contact with at least one of the first fluid or the second fluid, wherein the second electrode includes a dielectric coating.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A is a side cross-section view of an example eye-implantable device.

FIG. 2B is a side cross-section view of an example eye-implantable device shown in FIG. 2A.

DETAILED DESCRIPTION

Figure 1A:
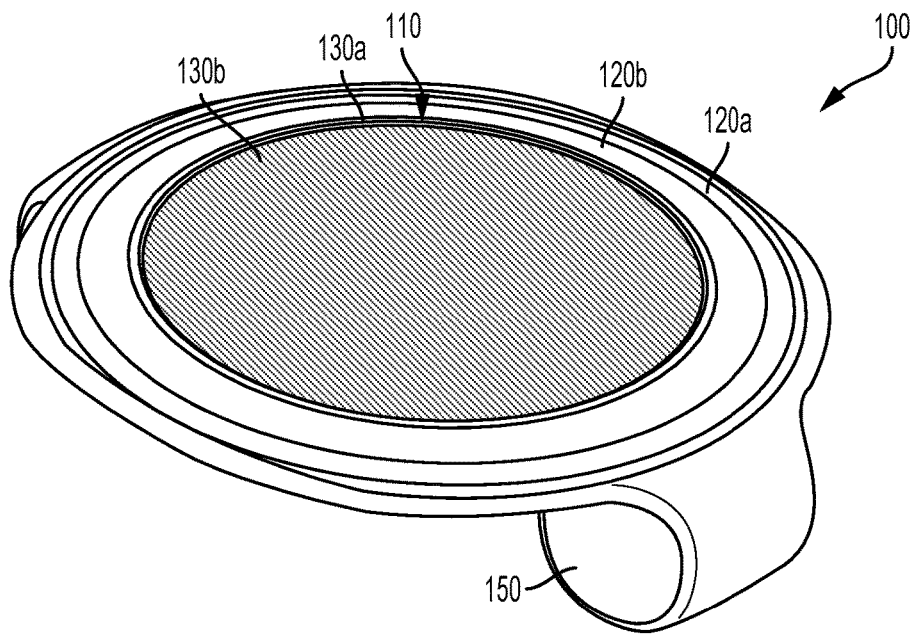
FIG. 1A is a perspective view of an example eye-implantable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Implantable devices could be located within the eye of a person to provide a static or adjustable optical power to the eye. Such a static or adjustable optical power could be provided to correct a lack or loss of optical power and/or accommodation in the eye, e.g., to correct for presbyopia, myopia, hyperopia, astigmatism, injury or damage to the eye, removal of the crystalline lens of the eye, or to correct for some other condition of the eye. Such implantable devices could be located within the lens capsule, within the anterior chamber, within the fibrous wall of the eye, proximate to the retina, or in some other location(s) of the eye according to an application. Such an eye-implantable device could include an electronically actuated lens to provide a controllable amount of optical power to the eye. An electronically actuated lens could include an electrowetting lens that includes two or more immiscible fluids whose geometry within the electrowetting lens can be electronically controlled (e.g., by applying an electrical voltage to two or more electrodes of the lens) in order to control an overall optical power of the electrowetting lens. Such an actuated lens could be configured in some other way to control an overall optical power of the lens, e.g., by pumping an amount of one or more immiscible fluids into or out of a lens chamber (e.g., via electrowetting or some other process).

The design and fabrication of such an eye-implantable device could be subject to a variety of mechanical, optical, electrical, chemical, and biochemical constraints. For example, materials of the eye-implantable device may be biocompatible, flexible (e.g., to permit folding or rolling in order to implant the device through a smaller incision), optically clear and/or having a specified refractive index, and/or have one or more further specified qualities. It may also be beneficial to fabricate such an eye-implantable device such that a lens chamber of a lens of the device is hermetically sealed. Such a hermetic seal could be provided to prevent water from passing between one or more aqueous fluids within the lens and the aqueous humor of the eye. Such passage of water could result in changes in the pressure and/or volume of the lens, causing damage to the lens, changes in the optical power of the lens, or other unwanted effects. It can be difficult to construct an eye-implantable device to maintain such a hermetic seal, to be able to be folded for implantation, to have one or more specified optical, mechanical, electrical, biochemical, or other properties, and/or to satisfy some additional constraints.

These constraints on the composition and/or configuration of an eye-implantable device could be relaxed by obviating the requirement that the lens chamber be hermetically sealed. Such a lens chamber, lacking a hermetic seal between the interior of the lens chamber and the environment of the lens chamber, may experience nets flows of water, ions, or other substances. Such flows may be related to differences in the concentration of such substances between the fluid(s) within the lens chamber and fluid(s) (e.g., aqueous humor) in the environment of the lens chamber (e.g., in a lens capsule of an eye). As noted above, it can be beneficial to prevent such flows, e.g., by specifying the composition of one or more fluids within the lens chamber (e.g., of a saline fluid within the lens chamber) such that the one or more fluids are matched to the aqueous humor with respect to osmolality, the concentration of one or more dissolved substances, or some other properties.

For example, the aqueous fluid(s) of a lens could have an osmolality that is substantially isotonic with the aqueous humor of the eye. As a result, the net flow of water into or out of the aqueous fluid of such a lens may be substantially zero. In such an example, the lens chamber of the lens may be made permeable to water or otherwise non-hermetic. This could include constructing the lens chamber from water-permeable materials (e.g., flexible, optically clear, and biocompatible water-permeable materials), using water-permeable sealant materials to form the device, and/or forming the device to include channels or other features that permit fluids to flow into or out of the lens chamber of the lens. Additionally or alternatively, the eye-implantable device could be fabricated such that cracks, channels, or other features in the seals or materials of the lens chamber are allowed to form during implantation or at other points in time (e.g., due to flexion, folding, rolling, or other mechanical manipulation of the eye-implantable device during implantation) that permit the flow of water into or out of the lens chamber of the lens, rendering the lens chamber permeable to water in the aqueous humor.

The osmolality of the aqueous fluid of the lens could correspond to the osmolality of the aqueous humor in a particular person or to an average osmolality of aqueous humor across a group of people. The osmolality of the aqueous fluid of the lens could be controlled by adding substances to the aqueous fluid, e.g., salts, proteins, albumin, or surfactants. In some examples, the lens chamber of the lens could be permeable to one or more of the substances in the aqueous fluid, and the lens chamber could be made impermeable to the one or more substances, e.g., to prevent the one or more substances from passing between the inside of the lens and aqueous humor surrounding the eye-implantable device. Additionally or alternatively, the concentration of such substances in the aqueous fluid of the lens chamber could be specified to correspond to the concentration of the substances in the aqueous humor, e.g., to prevent the concentration of the substances in the aqueous fluid from changing as the substances pass between the aqueous humor and the inside of the lens chamber.

Such eye-implantable devices could include electronics, antennas, voltage regulators, batteries, photovoltaic cells, sensors, or other elements to facilitate operations of the device, e.g., to provide a controllable optical power to an eye. Such eye-implantable devices could receive, from outside of the eye, radio frequency, optical, infrared, acoustic, or other forms of power to power the operations of the device, e.g., from a contact lens, eyeglasses, a head-mountable device, or some other source. The eye-implantable device could receive wireless transmissions to specify an amount of optical power to provide, via controlling the optical power of the lens, to the eye, could operate a sensor to detect a physical variable (e.g., an accommodation force exerted by ciliary muscles of the eye) to specify the amount of optical power to provide, or the eye-implantable device could use some additional or alternative source of information or commands to determine an amount of optical power to provide to an eye.

II. Example Eye-Implantable Device

An eye-implantable device (e.g., an intraocular lens, or IOL) can include electronics and an electronically actuated lens that are operable to provide a controllable optical power (e.g., a controllable diopter, focal length, or other form of optical power or refractive property) to an eye in which the device is implanted. Such an eye-implantable device could include haptics or other formed features, or be formed according to a particular shape, such that the eye-implantable device can be implanted in or at a particular location within an eye, e.g., within the lens capsule of the eye following removal of the crystalline lens, within the anterior chamber of the eye, within the posterior chamber of the eye, along an optical axis of the eye. A controller, battery, antenna, sensors, or other elements can be provided to power the device, to determine a specified amount of optical power to provide to the eye (e.g., based on a sensor output, based on a received wireless command), and to operate the electronically actuated lens to provide such a specified optical power by applying a voltage, current, or other electrical signal to the electronically actuated lens. In some examples, the electronically actuated lens could be an electrowetting lens.

Note that, while reference is made throughout this application to electrowetting lenses of eye-implantable devices, the embodiments provided herein could be applied to other applications. For example, isotonic fluids could be provided as part of a flexible lens of an eye-implantable device that is configured to control an optical power of the lens via some process other than or in addition to electrowetting. Such a device could be configured to pump one or more immiscible fluids into or out of a lens chamber of a lens using a piezo actuator, a electrowetting actuator, a shape-memory actuator, or other actuator to pump the one or more fluids into or out of the lens chamber.

Figure 1B:
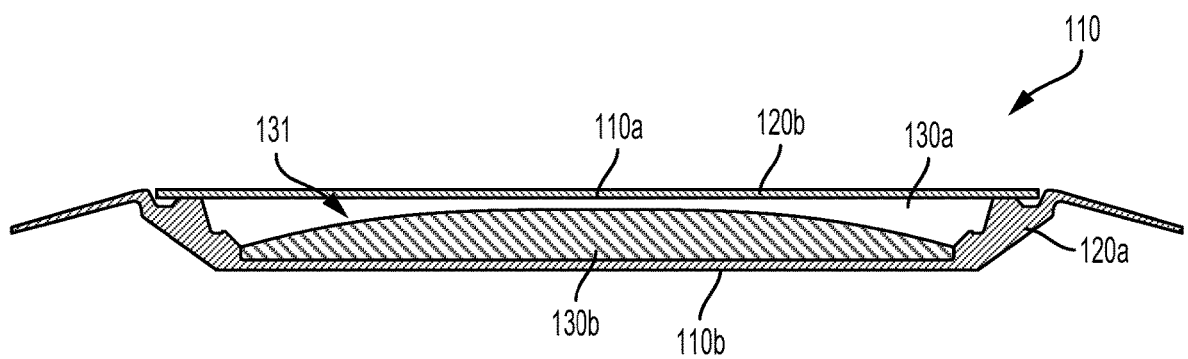
FIG. 1B is a side cross-section view of an electrowetting lens of the example eye-implantable device shown in FIG. 1A.

FIG. 1A is a bottom view of an example eye-implantable device 100. FIG. 1B is a cross-sectional view of an electrowetting lens 110 of the example eye-implantable device 100 shown in FIG. 1A. It is noted that relative dimensions in FIGS. 1A and 1B are not necessarily to scale, but have been rendered for purposes of explanation only in describing the arrangement of the example eye-implantable device 100 and electrowetting lens 110 thereof. The eye-implantable device 100 includes electronics 150 configured to operate the electrowetting lens 110 to provide a controllable optical power and to provide other operations of the eye-implantable device 100. The electronics 150 may include controllers, voltage regulators, antennas, photovoltaic cells, sensors, electrodes, transmitters, receivers, batteries, or other components. The electronics 150 may be configured to receive and/or store wireless energy to power the device 100 (e.g., visible light energy, infrared light energy, radio frequency electromagnetic energy, acoustic energy), to communicate with external devices or systems (e.g., to receive program updates, to receive a commanded optical power level), to detect one or more physical variables (e.g., a light level, a pupil diameter, an intraocular pressure, a voltage related to activity of muscles of the eye, a force exerted by ciliary muscles of the eye, a concentration of one or more substances in the eye) that may be used to determine an optical power to provide or that may be used in some other way, to operate the electrowetting lens 110, or to facilitate some other applications of the device 100.

The electrowetting lens 110 and/or other elements of the eye-implantable device 100 may be formed of one or more polymeric materials. The polymeric materials can include substantially transparent materials to allow incident light to be transmitted to the retina of the eye through the electrowetting lens 110 of the eye-implantable device 100. The polymeric materials can include biocompatible materials similar to those employed to form implants, vision correction lenses, IOLs, or other implantable devices, such as polyethylene terephthalate ("PET"), polymethyl methacrylate ("PMMA"), silicone hydrogels, rigid, gas-permeable polymeric materials, combinations of these, etc. The polymeric materials could include flexible and/or foldable water-permeable materials. For example, the polymeric material could include a copolymer comprising 2-phenylethyl acrylate units and 2-phenylethyl methacrylate units. Units of a polymer or copolymer could be cross-linked by an applicable cross-linking agent or unit, e.g., by 1,4-butanediol diacrylate units, 1,6-hexanediol diacrylate units, or some other crosslinking agent or combination of such agents. Such flexible and/or foldable materials may be included in the construction of the device 100 to permit the device 100 to be rolled, folded, or otherwise manipulated such that the device 100 may be inserted through an incision that is smaller than, e.g., the diameter of the unrolled or un-folded electrowetting lens 110. The eye-implantable device 100 may include coating materials disposed on one or more external or internal surfaces of the device, e.g., to improve a biocompatibility of the device, to control a surface energy of an internal surface of the electrowetting lens (e.g., to encourage or prevent wetting of a surface within a lens chamber by one or more fluids within the lens chamber), to prevent to passage of ions or other substances, or to provide some other benefit.

The electrowetting lens 110 includes a lens chamber 131 in which are disposed a first fluid 130a and a second fluid 130b. The lens chamber 131 is defined by first 120a and second 120b elements formed, respectively, as a cup and a flat lid. At least a portion of the first 120a and/or second 120b elements of the electrowetting lens 110 could be formed from a polymeric material (e.g., one of the polymeric materials listed elsewhere herein) that is permeable to water in aqueous humor of an eye (e.g., from a copolymer comprising 2-phenylethyl acrylate units and 2-phenylethyl methacrylate units cross-linked by 1,4-butanediol diacrylate units). Such a water-permeable polymeric material, or other polymeric or non-polymeric materials of the electrowetting lens 110, could be flexible such that the electrowetting lens 110 can be rolled, folded, or otherwise manipulated, e.g., to facilitate insertion through an incision in an eye. Additionally or alternatively, one or more sealant materials (e.g., a sealant material used to adhere the first element 120a to the second element 120b) of the electrowetting lens 110 could be permeable to water in aqueous humor of an eye.

Note that the illustrated first 120a and second 120b elements of the chamber 131 of the electrowetting lens 110 are intended as non-limiting example embodiments. For example, an electrowetting lens and/or a lens chamber thereof as described herein could be constructed from and/or defined by more or fewer elements (e.g., from a front element, a rear element, and an annular element) than the two shown and/or could be constructed from elements configured differently from the elements 120a, 120b illustrated here.

The first 130a and second 130b fluid are immiscible (e.g., the first fluid 130a could be saline or some other aqueous fluid and the second fluid 130b could be an oil or some other nonpolar fluid) and differ with respect to refractive index. Thus, a surface of contact between the first 130a and second 130b fluids (e.g., a convex shape, as shown in FIG. 1B) could provide an optical power (e.g., a diopter, a nonzero focal length) related to the difference in the refractive indices of the fluids 130a, 130b and the shape of the surface of contact. The electrowetting lens 110 further includes at least two electrodes (not shown) disposed on respective internal surface of the lens chamber 131. Voltages, currents, or other electrical signals can be applied to the at least two electrodes to electronically control the shape of the first 130a and second 130b fluids (e.g., to control a shape of a contact surface between the two fluids 130a, 130b) in order to control an optical power of the electrowetting lens 110.

One of the first 130a or second 130b fluid may include an aqueous solution. Such an aqueous solution may be substantially isotonic relative to the aqueous humor of an eye into which the eye-implantable device 100 is implanted. The aqueous solution could have an osmolality corresponding to the osmolality of the aqueous humor such that, if the lens chamber is permeable to water in the aqueous humor, a small or substantially zero amount of net water flow occurs between the aqueous solution within the lens chamber and the aqueous humor of the eye.

As the osmolality of aqueous humor is greater than the osmolality of blood, such an aqueous solution (e.g., an aqueous solution of the first fluid 130a) may have an osmolality that is higher than the osmolality of blood, e.g., an osmolality greater than 297 milliosmoles per kilogram. The aqueous solution may have an osmolality that is within a range of osmolalities that encompasses the osmolality of aqueous humor. For example, the aqueous fluid could have an osmolality between 300 milliosmoles per kilogram and 308 milliosmoles per kilogram. In another example, the aqueous fluid could have an osmolality between 302 milliosmoles per kilogram and 306 milliosmoles per kilogram.

The width of such a range of osmolalities, or the boundaries of such a range of osmolalities, could be related to an acceptable amount of net volume change within a lens chamber of an electrowetting lens (or within some other enclosure containing the aqueous solution). That is, the osmolality could be specified within a range of osmolalities such that, if the actual osmolality of the aqueous solution differs from the osmolality of the aqueous humor, a resulting amount of net water flow into (or out of) the lens chamber results in a volume change of the lens chamber, a mechanical deformation of the lens chamber, a change in the overall optical power of the electrowetting lens and/or an extent of an electronically controllable range of optical powers of the electrowetting lens, or some other factor(s) satisfy a constraint related to the functionality or standards-compliance of the eye-implantable device 100.

The overall optical power provided by the eye-implantable device 100 and/or the electrowetting lens 110 (e.g., to an eye in which the device 100 is implanted) could be related to the geometry, refractive index, or other properties of elements of the eye-implantable device 100. As noted above, this could include the shape of a contact surface between the first 130a and second 130b fluids within the lens chamber 131 and the refractive indices of the fluids 130a, 130b.

Other elements of the eye-implantable device 100 could provide a static and/or controllable optical power. For example, the front and/or rear surfaces of the electrowetting lens 110 could have curved surfaces to provide an optical power related to a change in refractive index between materials on either side of those surfaces (e.g., between a polymeric material of the first 120a and/or second 120b elements and aqueous humor of an eye, or between the polymeric material and one of the first 130a or second 130b fluids).

Components of the eye-implantable device 100 and/or electrowetting lens 110 (e.g., the first 120a or second 120b elements defining the lens chamber 131) can be formed to have a curved shape in a variety of ways. For example, techniques similar to those employed to form vision-correction contact lenses and/or intraocular lenses, such as heat molding, injection molding, spin casting, etc. can be employed to form polymeric materials into components of the eye-implantable device 100. Further, an eye-implantable device as described herein could have a different shape from that of the illustrated eye-implantable device 100. For example, an eye-implantable device could include haptics or other formed elements to maintain the eye-implantable device at a particular location within an eye (e.g., within a lens capsule of an eye), to detect accommodation forces exerted by ciliary muscles of an eye, or to provide some other benefit.

Figure 1C:
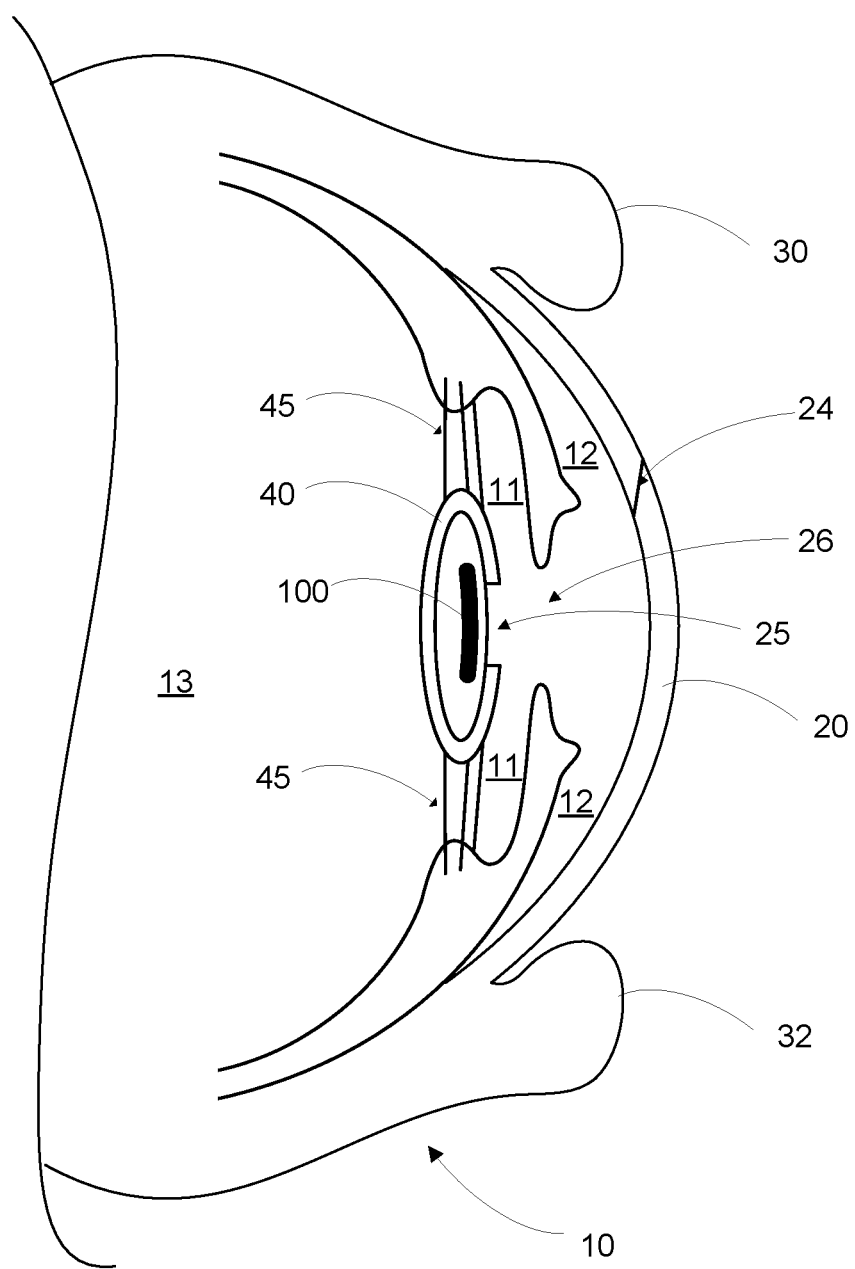
FIG. 1C is a side cross-section view of the example eye-implantable device shown in FIGS. 1A and 1B located within an eye.

FIG. 1C is a side cross-section view of the example eye-implantable device 100 while implanted within an eye 10. The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception.

The light received by the retina is transmitted, in the unaltered eye, through the crystalline lens, being refracted by the lens such that light received from the environment arrives in focus at the retina. The crystalline lens is located within the lens capsule 40 of the eye, which is connected, via the zonules 45, to accommodation muscles (e.g., ciliary muscles) and other elements of the eye. Accommodation forces transmitted through the zonules (e.g., forces generated by the accommodation muscles, forces generated by intrinsic elasticity of the zonules, or forces generated by other sources) act, in the eye, to deform the crystalline lens within the lens capsule 40, controlling the optical power provided by the crystalline lens.

As shown in FIG. 1C, the crystalline lens of the eye 10 has been removed and the eye-implantable device 100 has been surgically emplaced within the lens capsule 40 such that light received by the retina is transmitted through the electrowetting lens 110 of the eye-implantable device 100, being refracted by the electrowetting lens 110 and/or other elements of the eye-implantable device 100. Thus, the eye-implantable device 100 can be operated such that light received from the environment may arrive in focus at the retina, e.g., by operating the electrowetting lens 110 to provide a specified optical power.

The eye-implantable device 100 has been inserted into the eye 10 through an incision 24 formed in the cornea 20 of the eye 10 and then positioned within the lens capsule 40. In order to position the device 100 within the lens capsule 40, a hole 25 has been formed in the lens capsule 40 (e.g., via continuous curvilinear capsulorhexis) and the crystalline lens has been removed (e.g., via ultrasonic phacoemulsification). An eye-implantable device as described herein may be positioned in alternative locations within the eye 10, e.g., within the posterior chamber 11, anterior chamber 12, or in the vitreous humor 13 of the eye 10.

It is noted that relative dimensions in FIG. 1C are not necessarily to scale, but have been rendered for purposes of explanation only in describing the arrangement of the example eye-implantable device 100 within the eye 10. Further, such an implanted device could include multiple elements, located, e.g., in multiple different locations. Such multiple elements could be connected via a cable or by some other means. For example, such an implanted device could include a power reception element and controller that is disposed in the posterior capsule 11 and that is operable to receive wireless power from an eye-mountable device or other external system (not shown) and an electrowetting lens that is disposed within the lens capsule 40 could be operated, by the controller, via a tether connecting the controller and the electrowetting lens, using power from the power reception element.

The eye-implantable device 100 may be rollable, foldable, or otherwise flexible to permit its being rolled, folded, or otherwise manipulated into a smaller shape. This could permit the device 100 to be inserted through a smaller incision through the cornea 20. For example, the device 100 could be rolled up, folded in half, folded in thirds, or manipulated in some other way to permit the device 100 to be inserted through an incision 24 that is less than four millimeters long. In some examples, the device 100 may be rollable, foldable, or otherwise manipulable such that it can be inserted through an incision 24 that is less than 2 millimeters long. In such examples, the eye-implantable device 100 may be unrolled, unfolded, or otherwise manipulated into an operation shape or state (e.g., a substantially flat state) after it is inserted through the incision 24 in the cornea 20 and/or after it has been inserted through some other formed hole or incision (e.g., the hole 25 in the lens capsule) or through some other opening or feature of the eye (e.g., the pupil 26 of the eye 10) to position the device 100 in a specified location of the eye 10.

Note that, while the electrowetting lens 110 is illustrated as containing two fluids 130a, 130b, an electrowetting lens as described herein could be manufactured and distributed containing only one fluid (e.g., a fluid that includes an aqueous solution having an osmolality corresponding to the osmolality of aqueous humor). A second fluid (e.g., an oil or other nonpolar fluid) could later be added to the electrowetting lens. Such an electrowetting lens containing only a single fluid could be provided to simplify implantation or fabrication of the electrowetting lens. For example, by folding such an electrowetting lens, inserting it into position in an eye, and unfolding the lens before addition of the second fluid, fouling and/or wetting of internal surfaces of the electrowetting lens by the second fluid (e.g., due to the second fluid contacting the internal surfaces as a result of folding, bending, or otherwise manipulating the electrowetting lens during implantation) can be avoided. The second fluid can then be added after the electrowetting lens has been unfolded (e.g., via injection through a septum of the electrowetting lens using a needle, via a tubule connected to the electrowetting lens).

An electrowetting lens (e.g., 110) as described herein may be configured in a variety of ways such that a shape of two or more fluids (e.g., a polar fluid and a nonpolar fluid) can be controlled by the application of a voltage, current, or other electrical signal to electrodes of the electrowetting lens. In some examples, this could include applying, via the electrodes, an electrical field that changes the effective surface energy, surface tension, interfacial energy, or other surface properties of one or more surfaces within a lens chamber of the electrowetting lens such that a first one of the immiscible fluids retreats or advances across the one or more surfaces. As the first fluid retreats or advances across the one or more surfaces, the overall shape of the first fluid, and of a contact surface between the first fluid and a second fluid that is immiscible with the first fluid, may change. If the first fluid and second fluid have differing refractive indices, light may be refracted when passing through the electrowetting lens and an amount of that refraction (and a corresponding optical power of the electrowetting lens) could be related to the shape of the contact surface. Thus, the overall optical power of the electrowetting lens can be electronically controlled by applying electrical signals to the electrodes of the electrowetting lens to, e.g., control the shape of one or more fluids within the electrowetting lens and/or to control a shape of a contact surface between such fluids of the electrowetting lens.

FIG. 2A illustrates a cross-sectional view of an example electrowetting lens 200 during a first period of time. The electrowetting lens 200 includes a lens chamber 201 defined by first 210a and second 210b elements. In the example electrowetting lens 200, the lens chamber 201 is radially symmetric about a center line 202. A first electrode 220a is formed along a first internal surface 244a of the lens chamber 201 and takes the form of an inclined ring. A second electrode 220b is formed along a second internal surface 240b of the lens chamber 201. A first fluid 230a is disposed within the lens chamber 201 and, during the first period of time illustrated in FIG. 2A, is in contact with the first internal surface 240a, the first electrode 240a, a third internal surface 242a, and a fourth internal surface 244a of the lens chamber 201. A second fluid 230b is also disposed within the lens chamber 201 and is, during the first period of time, in contact with the second internal surface 240b and the second electrode 220b. During the first period of time, a contact surface between the first fluid 230a and the second fluid 230b has a first shape 235a. The first 230a and second 230b fluids are immiscible (e.g., the first fluid 230a is a nonpolar fluid and the second fluid 230b is a polar fluid) and have differing refractive indices.

As the first 230a and second 230b fluids differ with respect to refractive index, light that passes through the contact surface (e.g., light that is passing through the electrowetting lens 200 along the center line 202) may be refracted. A degree or amount of the refraction, and a related optical power of the electrowetting lens 200, may be related to the shape of the contact surface between the first fluid 230a and the second fluid 230b The shape of the contact surface can be controlled by applying an electrical signal to the electrodes 220a, 220b, e.g., by applying an electrical voltage to the electrodes 240a, 240b. There could be a relationship between the voltage applied to the electrodes 240a, 240b and the steady-state (e.g., following any transient changes in the electrowetting lens resulting from changes in the applied voltage) optical power of the electrowetting lens 200 and/or the shape of the contact surface between the fluids 230a, 230b. Such a relationship could be related to an effect on the surface energy of the first internal surface 240a relative to each of the fluids 230a, 230b, to an effective capacitance between the first electrode 220a and the second electrode 220a via a conductive second fluid 230b (e.g., via a second fluid 230 that includes a conductive, aqueous solution and that is in conductive and/or capacitive electrical contact with the second electrode 220b), or to some other factors.

The first electrode 220a and second electrode 220b could include conductive materials (e.g., aluminum, gold, copper, or other materials) disposed on respective internal surfaces of the lens chamber 201 (e.g., on surfaces of the first element 210a and second element 210b, respectively). Such deposition could include forming the electrodes in place (e.g., by sputtering, chemical vapor deposition, polymerization, deposition of a carrier fluid containing nanowires or other materials in suspension followed by evaporation of the carrier fluid, by photolithography or other processes for patterning or etching materials in place) and/or forming the electrodes and subsequently disposing them on internal surfaces of the lens chamber 201 (e.g., by using an adhesive to adhere a metal foil, wire, rod, cone, textured surface, or other formed conductive material to a surface within the lens chamber 201). Additionally or alternatively, one or both of the electrodes 220a, 220b could include wires, rods, cones, textured surfaces, or other elements that are disposed on and/or that penetrate through the internal surface of the lens chamber 201 and that protrude into the lens chamber 201.

One or both of the electrodes could further include a dielectric layer disposed between such a conductive material and the inside of the lens chamber 201. For example, the first electrode 220a could include such a dielectric layer. Such a dielectric layer could be provided to prevent large, direct currents from passing from the first electrode 220a into one or both of the first 230a or second 230b fluids, to provide a capacitive electrical coupling between the first electrode 220a and such fluids, to limit an amount of charge that can be transmitting into such fluids via the first electrode 220a, or to provide some other benefits.

Such a dielectric layer could be a separate material (e.g., parylene) deposited on the conductive material (e.g., via CVD, spin coating, or some other process). Additionally or alternatively, the dielectric layer of the first electrode 220a could be formed from the conductive material of the electrode, e.g., the dielectric layer could be a nonconductive layer of aluminum oxide formed by oxidation of an underlying aluminum metal of the first electrode 220a. Such a dielectric layer could be formed via anodization or other electrically-driven reactions at the surface of the electrode. Additionally or alternatively, such a dielectric layer could be formed by redox reactions between the fluids in the lens chamber 201 and the material of the electrode.

In some examples, the formation and/or maintenance of such a dielectric layer could be negatively impacted by the presence of certain ions within the lens chamber 201 (e.g., dissolved in one or both of the fluids 230a, 230b). For example, the presence of chloride ions could act to pit or otherwise damage a dielectric layer of aluminum oxide that has formed on the surface of an aluminum electrode. In such examples, a barrier could be formed from a chloride-impermeable material to prevent chloride ions present in the aqueous humor (or in some other environment to which the lens 200 is exposed) from entering the lens chamber 201 or from entering some other material or volume of the lens 200. Such a material could include a polymeric material, a metal foil or deposited metal layer, or some other material(s). Such materials could be substantially transparent to visible light.

The voltage between the electrodes 220a, 220b could be controlled in order to control the optical power of the electrowetting lens 200 by controlling the shape of the contact surface between the fluids 230a, 230b. FIG. 2B illustrates the electrowetting lens 200 during a second period of time during which a voltage is being applied to the electrodes 220a, 220b such that the contact surface between the first fluid 230a and the second fluid 230b has a second shape 235b. As a result, the optical power of the electrowetting lens 200 during the second period of time is different than the optical power of the electrowetting lens 200 during the first period of time.

The particular shape of the contact surface and/or of the geometry of the fluids 230a, 230b could be related to the applied voltage and to a variety of other factors. Such factors could include the interfacial energy between the fluids 230a, 230b, the interfacial energy between the fluids 230a, 230b and the internal surfaces 240a, 242a, 244a, 240b, the geometry of the internal surfaces 240a, 242a, 244a, 240b, a geometry of the electrodes 220a, 220b, and/or a geometry of a dielectric layer of the first electrode 220a. One or more of these factors could be specified in order to affect the shape of the contact surface between the fluids 230a, 230b, to affect the geometry and/or location of the fluids 230a, 230b within the lens chamber 201, to affect the relationship between an applied voltage and the optical power of the electrowetting lens 200, or to affect some other property of interest of the electrowetting lens 200.

This could include adding surfactants, polar and/or ionic substances, nonpolar substances, to the fluid(s) or otherwise specifying a composition of the first 230a and/or second 230b fluids to control an interfacial energy between the fluids 230a, 230b and/or to control an interfacial energy between the fluids and the internal surfaces 240a, 242a, 244a, 240b of the lens chamber. Additionally or alternatively, the composition of the material composing the internal surfaces 240a, 242a, 244a, 240b could be specified to control the interfacial energy between the internal surfaces and the fluids.

This could include selecting the bulk materials of the first 210a and second 210b elements and/or providing one or more coatings or surface treatments to the internal surfaces of the lens chamber 201. For example, the first fluid 230a could be an oil or other nonpolar fluid and one or more of the first 240a, third 242a, or fourth 244a internal surfaces could be superhydrophobic or otherwise hydrophobic. Further, the second fluid 230b could be a polar fluid (e.g., could include a saline solution or other aqueous solution having an osmolality corresponding to the osmolality of human aqueous humor) and the second 240b internal surface could be superhydrophilic or otherwise hydrophilic (e.g., by including a surface coating, by including a surface features or textures, by having been exposed to an oxidization process, or by some other means).

The distribution of such coatings or materials on the internal surfaces of the lens chamber 201 and/or the geometry of such surfaces could be specified to center the first fluid 230a along the center line 202 or along some other specified axis of the electrowetting lens 200. This could include applying different coating or other material to internal surfaces according to distance from the center line 202. Additionally or alternatively, a thickness or other property of a dielectric of the first electrode 220a could vary according to distance from the center line 202 such that, when a voltage is applied between the electrodes 220a, 220b, electrical and/or interfacial forces applied to the first 230a and/or second 230b fluids tend to center the first fluid 230a along the center line 202 and/or to conform a boundary between the fluids 230a, 230b on the first internal surface 240a to a circle centered on the center line 202.

In examples wherein one of the fluids 230a, 230b includes an aqueous solution that is isotonic relative to the aqueous humor of the eye, the lens chamber 201 may be composed of, enclosed by, or otherwise defined by water-permeable materials or may otherwise permit the flow of water from the aqueous humor into the lens chamber 201 or vice versa. In such examples, the lens chamber may include one or more channels 235b that are in fluid communication with the lens chamber 201 and with an external environment (e.g., an aqueous humor within an eye) of the electrowetting lens 200. Such a channel could be formed in elements of the electrowetting lens 200 (e.g., 210a) in order to provide pressure relief, to allow the filling of one or both of the fluids 230a, 230b into the lens chamber 201 following implantation, or to provide some other benefit. Additionally or alternatively, the channel 235b could represent one or more cracks, voids, or other features formed in the materials or seals of the electrowetting lens 200, e.g., due to folding and unfolding of the lens or due to some other manipulation during implantation of an eye-implantable device that includes the electrowetting lens 200.

The electrowetting lens 200 also includes a septum 239b. A first side of the septum 239b is in fluid communication with the lens chamber 201 (e.g., via a channel) and a second side of the septum 230b is in fluid communication with an external environment (e.g., an aqueous humor within an eye) of the electrowetting lens 200. Such a septum may be provided to facilitate the use of a needle to add or subtract one or both of the fluids 230a, 230b following implantation of the electrowetting lens 200 into an eye. For example, the electrowetting lens 200 could lack the first fluid 230a and could be folded, implanted into an eye, and unfolded. Subsequently, a needle could penetrate the septum 239b and be used to add the first fluid 230a and/or to remove an amount of the second fluid 230b. Additionally or alternatively, such post-implantation fluid transfer could occur via tubules (not shown) that provide fluid communication between the lens chamber 201 (e.g., via the channel 235b) and reservoirs, pumps, valves, or other apparatus that can source and/or sink an amount of the first 230a or second 230b fluids. Such tubules could then be crimped, laser welded, cut, or otherwise removed.

The lens chamber 201 could be permeable to water or other substances (e.g., ions) in aqueous humor of an eye. This could include the lens chamber 201 being defined and/or enclosed at least partially by a polymeric material that is permeable to water (or other substances) in the aqueous humor. In examples wherein the lens chamber is permeable to a substance that is present in the aqueous humor, one or both of the fluids 230a, 230b could include a concentration of the substance corresponding to the concentration of the substance in the aqueous humor, e.g., to prevent a net flow of the substance from the aqueous humor into the lens chamber 201 or vice versa.

Additionally or alternatively, the lens chamber could be made impermeable to such substances in the aqueous humor. This could include constructing the lens chamber from materials that are impermeable to the substances. Additionally or alternatively, a barrier layer or coating could be formed from such impermeable materials to prevent the substances from entering the lens chamber 201 or some other element or structure of the electrowetting lens 200. For example, a barrier could be formed from a chloride-impermeable material to prevent chloride ions present in the aqueous humor from entering the lens chamber 201, the material of the septum 239b, or form entering some other material or volume of the lens 200. Such a material could include a polymeric material, a metal foil or deposited metal layer, or some other material(s). Such materials could be substantially transparent to visible light.

In some examples, the septum 239b or other components of the electrowetting lens 200 could be composed of a self-healing material. For example, the lens chamber 201 could be at least partially defined by self-healing materials. Such self-healing materials could be provided to maintain the integrity of the lens chamber 201 or of other volumes of the electrowetting lens 200 again bulk fluid flows into or out of such volumes (e.g., between the lens chamber 201 and the aqueous humor of an eye). In some examples, such self-healing materials may be degraded and/or their ability to self-heal diminished by exposure to chloride ions or other substances present in the aqueous humor and/or in the fluids 230a, 230b of the electrowetting lens 200. In such examples, an impermeable material (e.g., a chloride-impermeable material) could be used to form a barrier between the chloride ions or other substances present in the aqueous humor and the self-healing material.

III. Example Electronics of Devices

Figure 3:
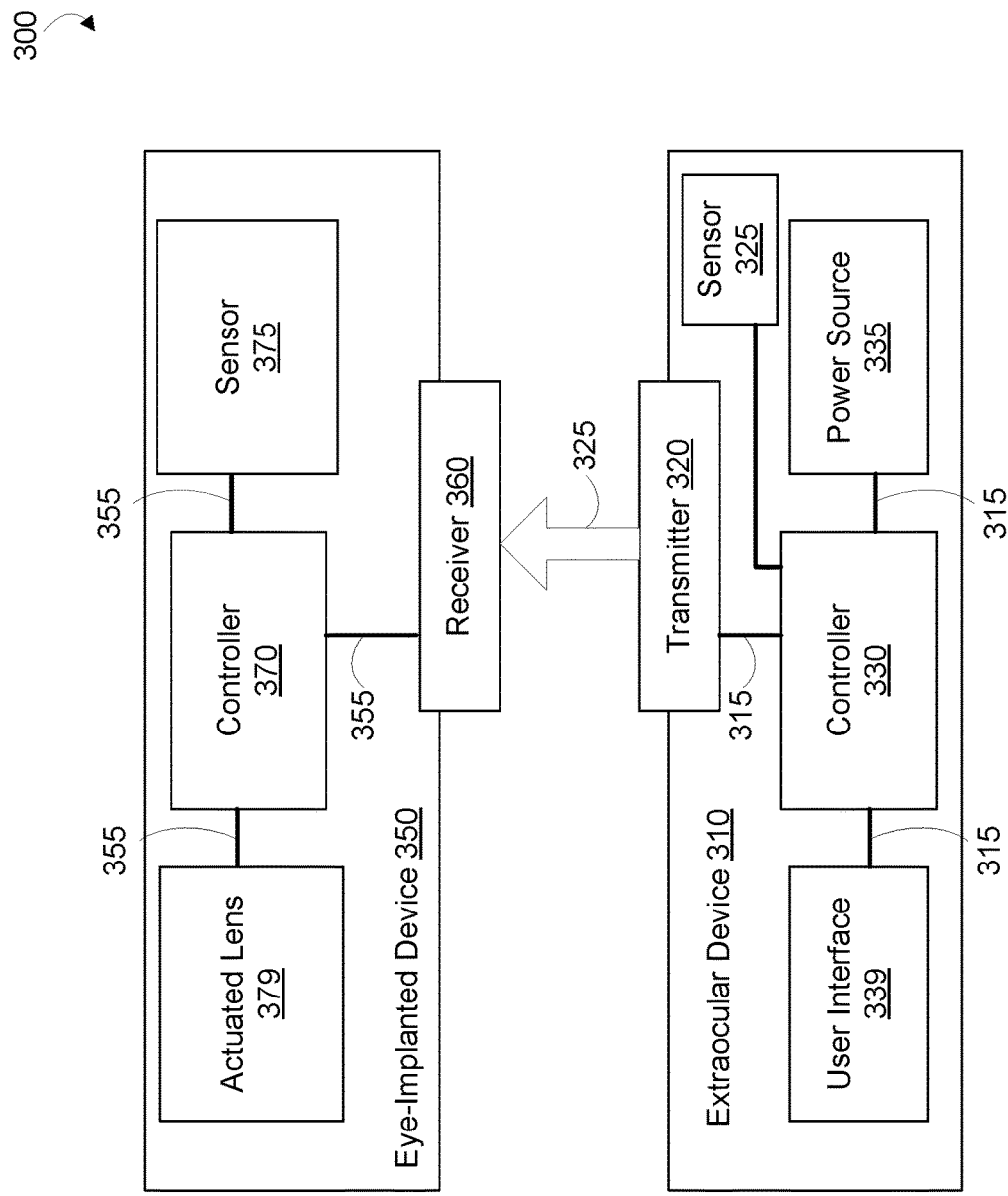
FIG. 3 is a block diagram of an example system that includes an extraocular device that can provide power to an eye-implanted device.

FIG. 3 is a block diagram of a system 300 that includes an extraocular device 310 wirelessly transmitting wireless signals 325 to an eye-implanted device 350. The wireless signals 325 may include wireless power signals to provide power to the eye-implanted device 350, control signals to control the operation of the eye-implanted device 350 (e.g., to control an optical power provided by an actuated lens 379 of the eye-implanted device 350), or other wireless signals. The extraocular device 310 may be a body-mounted device, e.g., a contact lens, a head-mounted display, or some other type of head-mounted device. Additionally or alternatively, the extraocular device 310 may be a handheld device like a cell phone, a device incorporated into furniture, e.g., into a bed to facilitate charging of the eye-implantable device 350 while a user sleeps, or may take some other form(s). The eye-implanted device 350 is implanted on or within an eye of a user.

The extraocular device 310 includes a controller 330, user interface 339, a transmitter 320, a power source 335, and a sensor 325. The transmitter 320 can be operated to wirelessly transmit power, commands, or other signals to the eye-implanted device 350 in an eye. The transmitter 320, the controller 330, the power source 335, the user interface 339, and the sensor 325 can all be connected together via interconnects 315, e.g., via wires, cables and/or, patterns of metallic traces formed on a printed circuit board or other substrate material on which the components may be disposed. Further, the transmitter 320 could comprise metallic traces or patterns formed on such a substrate material (e.g., to form antennas, impedance matching elements, plates of capacitors, electrodes, mirrors or diffraction gratings).

The transmitter 320 can include light-emitting elements (e.g., LEDs, lasers, VCSELs), radio-frequency electromagnetic energy-transmitting elements (e.g., antennas, coils), elements configured to inject a time-varying current into tissues or fluids of the body 501 (e.g., electrodes), or other elements configured to transmit, e.g., power from the power source 335 to the implanted device 350. The transmitter 320 could be configured to control an intensity, a phase, a frequency, a polarization, a direction, or some other properties of wireless signals transmitted from the transmitter 320 to indicate information. The transmitter 320 could be configured to provide power to the eye-implanted device 350 when the extraocular device 310 is not mounted to an eye or body of a user (e.g., when the user is sleeping in a bed such that the eye-implanted device 350 within an eye of the user is proximate to the extraocular device 310) or while the extraocular device 310 is mounted to the eye or body of the user.

The power source 335 may include a power receiver to provide power to the extraocular device 310 to, e.g., to recharge a rechargeable battery of the power source 335 in embodiments wherein the extraocular device 310 is an eye-mountable device. The power source 335 could include a battery (e.g., single-use alkaline batteries, rechargeable lithium-polymer batteries), a solar cell, connection to a mains power source, or some other source of energy.

The sensor 325 may be configured to detect physiological properties (e.g., a pupillary diameter of an eye), environmental parameters (e.g., an ambient light level, a distance between eyes of a user and an object at which the user is looking), to detect movements of the eye and/or eyelids of a user (e.g., to detect a vergence of the eyes), or to otherwise detect physical parameters that may be relevant to the operation of the extraocular device 310 and/or the eye-implanted device 350. The user interface 339 may include displays, inputs, speakers, microphones, touchscreens, buttons, scroll wheels, or other elements to facilitate receiving information (e.g., commands) from a user and/or to provide information (e.g., a command interface, a battery status or other information about the devices 310, 350) to a user. For example, the user interface 339 may be operated to receive commands from a user related to a desired optical power of the eye-implanted device 350 and/or information about a distance a user wishes to see or some other information related to an optical power that could be desired from the eye-implanted device 350.

The eye-implanted device 350 includes a controller 370, a sensor 375, a receiver 360, and an actuated lens 379. The actuated lens 379 could be an electrowetting lens as described herein. The receiver 360 can be operated to receive power or other wireless signals 325 wirelessly transmitted by the transmitter 320 (e.g., from the power source 335 of the extraocular device 310). This could include receiving optical signals (e.g., via a photovoltaic cell, photodiode, or other light-sensitive elements), radio frequency electromagnetic signals (e.g., via an antenna, via a coil), an electrical current or potential in the tissues or fluids surrounding the eye-implanted device 350 (e.g., via electrodes), or receiving some other signals wirelessly transmitted from the extraocular device 310. The eye-implanted device 350 could include an ultracapacitor or some other form of short-term energy storage to provide energy for use by the device 350 when power is unavailable from the other systems (e.g., when the extraocular device 310 is not mounted to or otherwise proximate to the eye-implanted device 350).

The sensor 375 is configured to detect a physiological property of the body (e.g., a pressure or force, a biopotential, a light intensity). In a particular example, the sensor 375 could be an accommodation sensor configured to detect, directly or indirectly, accommodation forces exerted on a lens capsule of the eye, e.g., by detecting a force or pressure within the lens capsule via haptics, via an elastic material disposed in the lens capsule, via detection of electrical activity of the ciliary muscles, or via some other means.

The actuated lens 379 is operable to control an optical power that is provided to the eye by the actuated lens 379. Operating the actuated lens 379 to control the optical power of the lens could include applying a voltage to a liquid crystal of the lens 379, applying a voltage to electrodes of an electrowetting actuated lens 379 or operating a pump or some other element to control a pressure and/or disposition of a fluid within the lens 379, or controlling the optical power of the lens by some other method.

The eye-implanted device 350 and/or extraocular device 310 could include additional or alternative elements, and could include more or fewer elements than those illustrated in FIG. 3. This could include the eye-implanted device 350 including elements configured to transmit wireless signals to the extraocular device 310 and the extraocular device 310 including elements configure to receive such transmitted signals. In such an example, the eye-implanted device 350 and the extraocular device 310 could additionally include a transmitter and receiver, respectively. Additionally or alternatively, the illustrated receiver 360 and transmitter 320 could be configured as transceivers to facilitate bidirectional communication and/or to share one or more elements (e.g., antennas, filters, coils, power conditioning systems) in common with other elements configured to facilitate bidirectional communication.

It is noted that the block diagram shown in FIG. 3 is described in connection with functional modules for convenience in description. However, embodiments of the extraocular device 310 and/or eye-implanted device 350 can be arranged with one or more of the functional modules ("sub-systems") implemented in a single chip, integrated circuit, and/or physical feature. That is, the functional blocks in FIG. 3 need not be implemented as separated modules. Moreover, one or more of the functional modules described in FIG. 3 can be implemented by separately packaged chips or other components electrically connected to one another. Further, note that an extraocular device and/or an eye-implantable device as described herein could include additional or alternative components to those shown in FIG. 3 (e.g., additional sensors, actuated lenses, displays, retinal stimulator arrays, electrodes, batteries, controllers, transmitters, receivers, stimulators, etc.). For example, the power source 335 of the extraocular device 310 could be a single-use battery and the extraocular device 310 could be operated as a single-use device (e.g., operated until the battery of the power source 335 is depleted and then discarded and/or recycled).

IV. Example Methods

Figure 4:
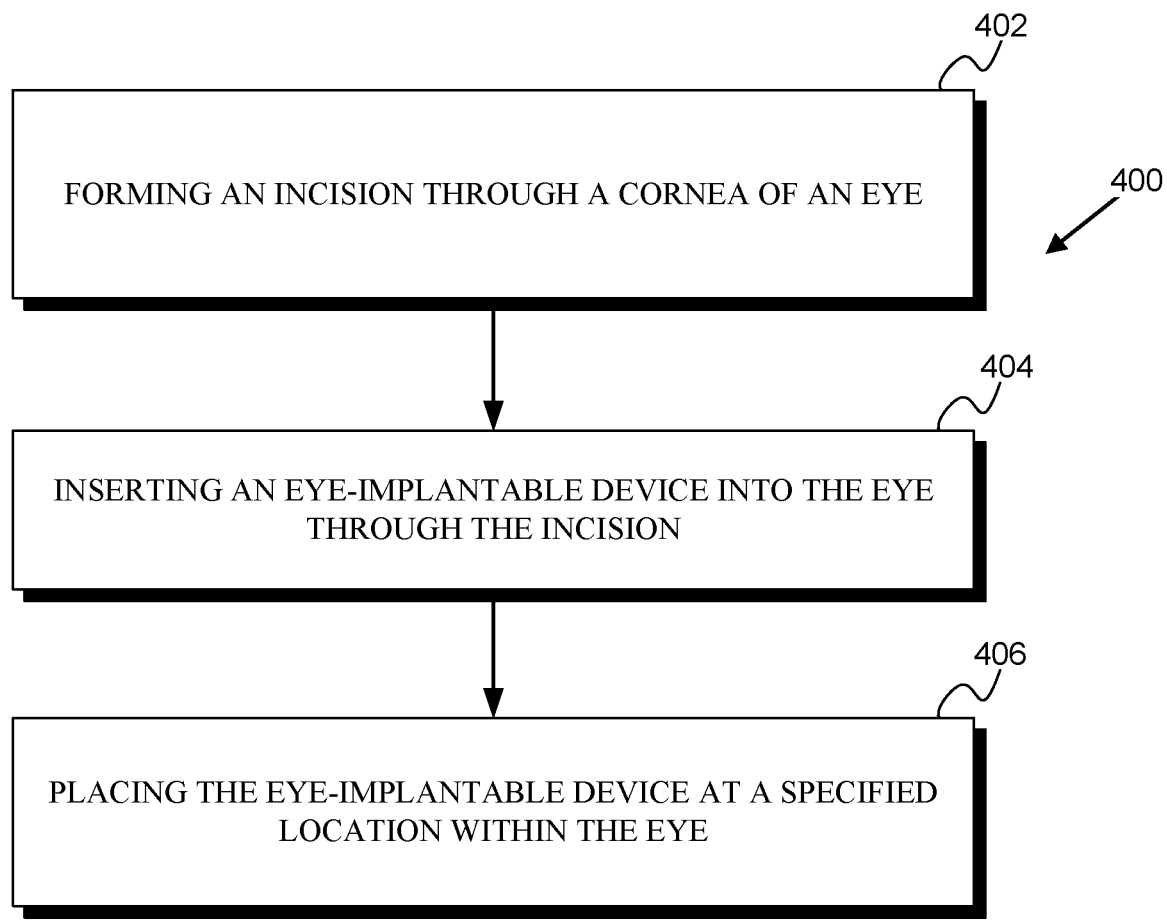
FIG. 4 is a flowchart of an example process.

FIG. 4 is a flowchart of a method 400 for implanting an eye-implantable device within a human eye. The device includes an electrowetting lens as described herein that includes (i) a polymeric material that is permeable to water in an aqueous humor of the eye, (ii) a lens chamber, at least a portion of which is defined by the polymeric material, (iii) a first fluid that is disposed within the lens chamber and that has an osmolality corresponding to an osmolality of the aqueous humor, (iv) a second fluid that is disposed within the lens chamber, that is immiscible with the first fluid, and that differs from the first fluid with respect to refractive index, (v) a first electrode that is disposed on an internal surface of the lens chamber in contact with the first fluid, and (vi) a second electrode that includes a dielectric coating and that is disposed on an internal surface of the lens chamber in contact with at least one of the first fluid or the second fluid.

The method 400 includes forming an incision through the cornea of the eye (402). This could include operating a scalpel, a laser, a diamond blade, a metal blade, or some other instruments to create an incision through the cornea. The incision could be created by creating multiple separate cuts or incisions into the cornea. For example, a first cut could be made perpendicular to the surface of the sclera, and one or more subsequent cuts could be made at other angles (e.g., tangential angles) relative to the sclera. The incision could be formed to be water-tight, to cause a minimum of astigmatism, or to satisfy some other considerations. The formation of the incision (402) could be accompanied by mechanical stabilization of the eye (e.g., using fixation rings, forceps, or other means), administration of topical or global anesthesia, or some other steps. The formed incision could have a length or other dimension within some specified range; e.g., the incision could be less than 4 millimeters long, or less than 2 millimeters long.

The method 400 includes inserting the eye-implantable device into the eye through the incision (404). This could include using forceps or some other means to insert the eye-implantable device through the incision. Additionally or alternatively, the eye-implantable device could include tabs, rods, or other features to facilitate such insertion. Such features could be later removed from the eye-implantable device (e.g., by cutting, crimping, laser cutting, or some other means) or could remain as part of the eye-implantable device following implantation.

The method 400 further includes placing the eye-implantable device at a specified location within the eye (406). As noted above for insertion of the eye-implantable device through the incision (404), this could include instruments to manipulate and position the eye-implantable device and/or using tabs, rods, or other features of the eye-implantable device. Placing the eye-implantable device at the specified location (406) could include inserting the device through additional incisions or other surgically formed features of the eye (e.g., an incision through the iris, through a hole formed in the lens capsule of the eye) and/or through natural features of the eye (e.g., through the pupil of the iris). The specified location could be within the lens capsule, in the anterior capsule, in the posterior capsule, in the vitreous humor, or in some other location of the eye. Placing the eye-implantable device at the specified location (406) could include manipulating haptics or other features of the device and/or additional implanted elements in order to secure the device at the specified location, to facilitate interactions between the device and the eye (e.g., to facilitate detection of accommodation forces applied to the lens capsule of the eye), or to provide some other benefit. Placing the eye-implantable device at the specified location (406) could include assembling multiple different elements of the device together, e.g., assembling an electrowetting lens together with an electronics module to form the eye-implantable device.

The method 400 could include additional steps or elements in addition to those depicted in FIG. 4 (i.e., 402, 404, 406). For example, the method 400 could include adding or removing material, e.g., adding or removing an amount of the first or second fluids, from the eye-implantable device. This could be performed using a needle (e.g., by piercing a septum of the device with the needle), using tubes connected between the device and external systems, or via some other method. In examples wherein tubes are used, the method 400 could further include severing such tubes (e.g., via mechanical and/or ultrasonic crimping and cutting, via mechanical cutting, via laser cutting, via application of a shearing or tension force to the tubes) and removing portions of the severed tubes from the eye. The method 400 could include further surgical manipulations of the eye, e.g., the formation of a hole in the lens capsule and/or the removal of the crystalline lens, the removal of a previously implanted device (e.g., a static IOL). The method 400 could include programming and/or testing the eye-implantable device. In some examples, the eye-implantable device could be rolled, folded, or otherwise manipulated to reduce one or more dimensions of the device (e.g., in order to facilitate insertion of the device through a smaller incision) and the method 400 could include unrolling, unfolding, or otherwise manipulating the eye-implantable device subsequent to inserting the device through the incision (404). In some examples, the eye-implantable device could be implanted through the sclera or via some other route, and the method 400 could include forming alternative incisions (e.g., through the sclera) and inserting the device through such alternative incisions.

Figure 5:
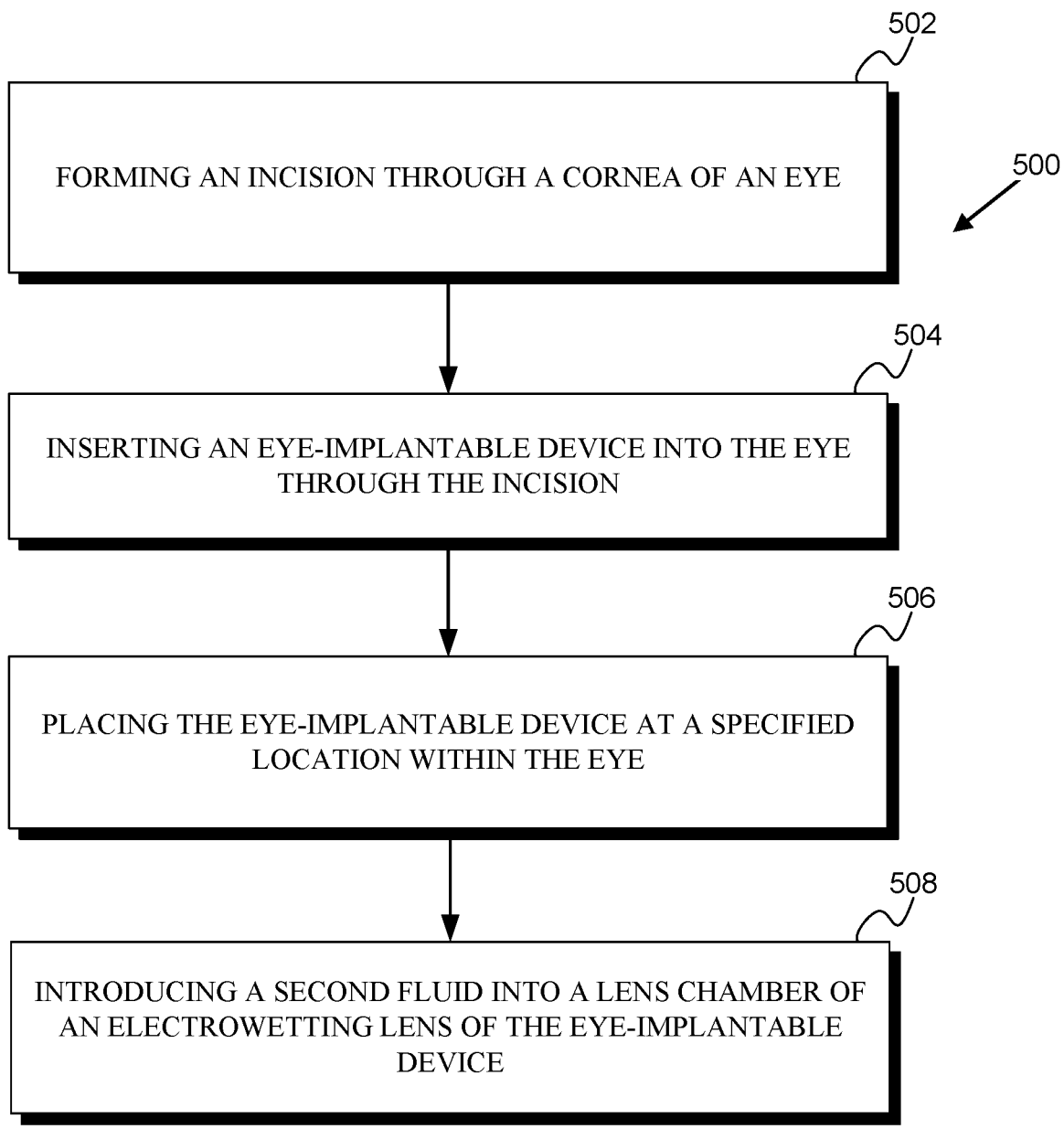
FIG. 5 is a flowchart of an example process.

FIG. 5 is a flowchart of a method 500 for implanting an eye-implantable device within a human eye. The device includes an electrowetting lens similar to that described in relation to method 400 that lacks the second fluid and that may be filled with the second fluid following implantation (e.g., to avoid fouling or wetting, by the second fluid, of one or more internal surfaces of a lens chamber of the electrowetting lens during implantation).

The method 500 includes forming an incision through the cornea of the eye (502), inserting the eye-implantable device into the eye through the incision (504), and placing the eye-implantable device at a specified location within the eye (506). These elements of the method 500 could be similar to corresponding elements of method 400 discussed above.

The method 500 further includes introducing a second fluid into the lens chamber of the electrowetting lens of the eye-implantable device (508). This could be performed using a needle (e.g., by piercing a septum of the device with the needle), using tubes connected between the device and external systems, or via some other method. In examples wherein tubes are used, the method 500 could further include severing such tubes (e.g., via mechanical and/or ultrasonic crimping and cutting, via mechanical cutting, via laser cutting, via application of a shearing or tension force to the tubes) and removing portions of the severed tubes from the eye.

The method 500 could include additional steps or elements in addition to those depicted in FIG. 5 (i.e., 502, 504, 506). For example, the method 500 could include adding or removing other material, e.g., adding or removing an amount of the first fluid, from the eye-implantable device. The method 500 could include further surgical manipulations of the eye. The method 500 could include programming and/or testing the eye-implantable device. In some examples, the eye-implantable device could be rolled, folded, or otherwise manipulated to reduce one or more dimensions of the device (e.g., in order to facilitate insertion of the device through a smaller incision) and the method 500 could include unrolling, unfolding, or otherwise manipulating the eye-implantable device subsequent to inserting the device through the incision (504). In some examples, the eye-implantable device could be implanted through the sclera or via some other route, and the method 500 could include forming alternative incisions (e.g., through the sclera) and inserting the device through such alternative incisions.

V. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. An eye-implantable device comprising:
   an electrowetting lens, wherein the electrowetting lens comprises:
   a polymeric material, wherein the polymeric material is permeable to water in an aqueous humor of a human eye;
   a lens chamber, wherein the polymeric material defines at least a portion of the lens chamber;
   a first fluid disposed in the lens chamber, wherein the first fluid comprises an aqueous solution having an osmolality between 300 and 308 milliosmoles per kilogram;
   a second fluid disposed in the lens chamber, wherein the second fluid is immiscible with the first fluid, and wherein a refractive index of the second fluid differs from a refractive index of the first fluid;
   a first electrode, wherein the first electrode is disposed on an internal surface of the lens chamber in contact with the first fluid; and
   a second electrode, wherein the second electrode is disposed on an internal surface of the lens chamber in contact with at least one of the first fluid or the second fluid, wherein the second electrode comprises a dielectric coating.

2. The eye-implantable device of claim 1, wherein the osmolality of the first fluid is between 302 milliosmoles per kilogram and 306 milliosmoles per kilogram.

3. The eye-implantable device of claim 1, wherein the polymeric material is flexible such that the electrowetting lens can be folded.

4. The eye-implantable device of claim 1, wherein the polymeric material comprises 2-phenylethyl acrylate units and 2-phenylethyl methacrylate units.

5. The eye-implantable device of claim 1, further comprising a channel, wherein the channel is in fluid communication with the lens chamber and an external environment of the eye-implantable device.

6. The eye-implantable device of claim 1, wherein the second electrode comprises aluminum metal, wherein the dielectric coating of the second electrode is formed from the aluminum of the second electrode via a reaction between the aluminum metal of the second electrode and at least one of the first fluid or the second fluid, wherein the eye-implantable device further comprises a chloride-impermeable material, wherein the chloride-impermeable material forms a barrier between chloride ions present in the aqueous humor and the dielectric coating of the second electrode.

7. The eye-implantable device of claim 1, further comprising a controller, wherein the controller comprises a voltage regulator that is electronically coupled to the first electrode and the second electrode, wherein the voltage regulator is operable to apply a voltage between the first electrode and the second electrode, wherein a geometry of an interface between the first fluid and the second fluid is related to the voltage applied between the first electrode and the second electrode, and wherein an optical power of the electrowetting lens is related to the geometry of the interface between the first fluid and the second fluid.

8. An eye-implantable device comprising:
   an electrowetting lens, wherein the electrowetting lens comprises:
   a polymeric material, wherein the polymeric material is permeable to water in an aqueous humor of a human eye;
   a lens chamber, wherein the polymeric material defines at least a portion of the lens chamber;
   a first fluid disposed in the lens chamber, wherein the first fluid comprises an aqueous solution having an osmolality between 300 and 308 milliosmoles per kilogram;
   a first electrode, wherein the first electrode is disposed on an internal surface of the lens chamber in contact with the first fluid; and
   a second electrode, wherein the second electrode is disposed on an internal surface of the lens chamber in contact with the first fluid, wherein the second electrode comprises a dielectric coating.

9. The eye-implantable device of claim 8, wherein the osmolality of the first fluid is between 302 milliosmoles per kilogram and 306 milliosmoles per kilogram.

10. The eye-implantable device of claim 8, wherein the polymeric material is flexible such that the electrowetting lens can be folded.

11. The eye-implantable device of claim 8, wherein the polymeric material comprises 2-phenylethyl acrylate units and 2-phenylethyl methacrylate units.

12. The eye-implantable device of claim 8, further comprising a channel, wherein the channel is in fluid communication with the lens chamber and an external environment of the eye-implantable device.

13. The eye-implantable device of claim 8, further comprising a septum, wherein a first side of the septum is in fluid communication with the lens chamber, and wherein a second side of the septum is in fluid communication with an external environment of the eye-implantable device.

14. A method comprising:
forming an incision through a cornea of an eye;
inserting an eye-implantable device into the eye through the incision; and
placing the eye-implantable device at a specified location within the eye, wherein the eye-implantable device comprises:
an electrowetting lens, wherein the electrowetting lens comprises:
a polymeric material, wherein the polymeric material is permeable to water in an aqueous humor of the eye;
a lens chamber, wherein the polymeric material defines at least a portion of the lens chamber;
a first fluid disposed in the lens chamber, wherein the first fluid comprises an aqueous solution having an osmolality between 300 and 308 milliosmoles per kilogram;
a second fluid disposed in the lens chamber, wherein the second fluid is immiscible with the first fluid, and wherein a refractive index of the second fluid differs from a refractive index of the first fluid;
a first electrode, wherein the first electrode is disposed on an internal surface of the lens chamber in contact with the first fluid; and
a second electrode, wherein the second electrode is disposed on an internal surface of the lens chamber in contact with at least one of the first fluid or the second fluid, wherein the second electrode comprises a dielectric coating.

15. The method of claim 14, wherein the specified location is a location within a lens capsule of the eye.

16. The method of claim 14, wherein the polymeric material is flexible such that the electrowetting lens can be folded, wherein inserting an eye-implantable device into the eye through the incision comprises inserting the eye-implantable device in a folded state, and further comprising:
subsequent to inserting the eye-implantable device into the eye through the incision, unfolding the electrowetting lens of the eye-implantable device.

17. The method of claim 16, wherein the incision is less than 4 millimeters long.

18. The method of claim 14, wherein the osmolality of the first fluid is between 302 milliosmoles per kilogram and 306 milliosmoles per kilogram.

* * * * *